United States Patent [19]
Boulton et al.

[11] Patent Number: 6,027,694
[45] Date of Patent: Feb. 22, 2000

[54] SPILLPROOF MICROPLATE ASSEMBLY

[75] Inventors: David A. Boulton; Carolyn I. Solewski, both of Tinton Falls, N.J.

[73] Assignee: Texperts, Inc., Tinton Falls, N.J.

[21] Appl. No.: 08/953,441

[22] Filed: Oct. 17, 1997

Related U.S. Application Data

[60] Provisional application No. 60/028,587, Oct. 17, 1996.

[51] Int. Cl.[7] .............................. B01L 11/00; B01L 3/14; B01D 29/00
[52] U.S. Cl. ..................... 422/102; 422/104; 435/288.4
[58] Field of Search .................... 422/102, 104, 422/99–101; 435/286.6, 288.2–288.4

[56] References Cited

U.S. PATENT DOCUMENTS

| | | |
|---|---|---|
| 86,670 | 2/1869 | Hickman . |
| 2,627,619 | 2/1953 | Gagen . |
| 4,024,857 | 5/1977 | Blecher et al. . |
| 4,070,249 | 1/1978 | Janin et al. . |
| 4,073,693 | 2/1978 | Janin . |
| 4,278,437 | 7/1981 | Haggar . |
| 4,286,637 | 9/1981 | Wilson . |
| 4,885,253 | 12/1989 | Kralovic ................................ 435/296 |
| 5,244,635 | 9/1993 | Rabson et al. . |
| 5,264,184 | 11/1993 | Aysta et al. ............................. 422/101 |
| 5,429,803 | 7/1995 | Guirguis ................................. 422/101 |

FOREIGN PATENT DOCUMENTS

| | | |
|---|---|---|
| 1109034 | 9/1981 | Canada . |
| 627 358 A1 | 12/1994 | European Pat. Off. . |
| WO 97/11939 | 7/1992 | WIPO . |

OTHER PUBLICATIONS

R.A. Zeineh, "Spillproof, disposable test tube", *American Laboratory*, vol. 8, No. 11, Nov. 1976, pp. 51–53.

T. Astle, "Setting a New Industry Standard that Accomodates Robotics", *Laboratory Automation News*, vol. 1, No. 2, Mar. 1996, pp. 24–26.

*Primary Examiner*—Lyle A. Alexander
*Attorney, Agent, or Firm*—Michaelson & Wallace; Peter L. Michaelson; Jeremiah G. Murray

[57] ABSTRACT

A microplate assembly comprising a multi-well microplate, a plurality of vent caps and a porous vent film. The microplate includes a frame that houses a plurality of open wells in a rectangular array. Vent caps mount on the microplate to seal and vent the wells. When the vent caps are coupled to the wells, an interior volume is formed in each well. The wells function as a vessel for liquid samples that occupy predetermined spaces within the interior volumes. The liquid samples remain within its predetermined space for all orientations of the microplate assembly. The vent cap comprises an array of well inserts. Each well insert comprises a sealing plug and a vent tube. The well inserts are interconnected by a perforated web. The sealing plugs form a seal at the mouth of the open wells. The vent tubes, which are fixed to the sealing plugs, terminate in a vent that communicates with the interior volumes outside the predetermined spaces occupied by the liquid samples. The vents permit the pressure within the interior volume to be equalized with the ambient pressure via a passage that runs through the vent tube and the sealing plugs. Material may be added to or removed from each well without removing the vent cap. The porous vent film, which has an adhesive coating, adheres to the vent caps while covering the passages, thereby inhibiting evaporation of the liquid samples.

19 Claims, 7 Drawing Sheets

SPILLPROOF MICROPLATE ASSEMBLY

CLAIM TO PRIORITY

This application is claiming priority to our U.S. provisional patent application entitled "SPILL-PROOF MICRO PLATE SYSTEM" filed Oct. 17, 1996 and assigned serial No. 60/028,587.

BACKGROUND OF THE INVENTION

1. Field of the Invention

The present invention relates generally to techniques for handling fluid samples in chemical, biological, pharmacological and related processes. More particularly, it relates to spillproof microplate apparatus for receiving and securely holding fluid samples.

2. Description of the Prior Art

Multi-well microplates play an important role in conventional chemical, biological, pharmacological and related processes that are designed to analyze and/or synthesize large numbers of small fluid samples. Such conventional processes normally employ multi-well microplates as tools when processing, shipping and storing the small liquid samples. Many of these processes achieve high-throughputs by applying modern automation techniques, including robotics. In recent years, efforts have been directed at integrating the different prevailing microplate apparatus into the automation equipment of these high-throughput processes. Such integration efforts, however, have had only limited success. Specifically, spillage, leakage, evaporation loss, airborne contamination and inter-well cross contamination of liquid samples are some of the common deficiencies that limit the application of many standard microplate assemblies in high-throughput systems. Consequently, one of the most critical problems confronting designers of microplate apparatus has been finding techniques of preventing the loss and contamination of well contents without unduly complicating the structures and/or handling requirements of a microplate assembly.

A standard microplate assembly normally comprises a microplate having a plurality of open wells and a closure device for sealing the wells shut. Commonly available microplates generally embody a unitary molded structure comprising a rigid frame for housing a plurality of open wells arranged in a rectangular array. Standard well closures include resilient, press-fit stoppers, rigid screw caps, adhesive films and the like. Microplates come in a range of sizes; a well may be sized to hold as high as five milliliters or as low as only a few microliters of liquid. In addition, microplates come in a variety of materials, such as polystyrene, polycarbonate, polypropylene, Teflon, glass, ceramics and quartz. Conventional microplates found in many high-throughput systems comprise a 96-well geometry molded into an 8×12 rectangular array of open wells. Microplates with lower well densities (e.g., 24 and 48 wells) and higher well densities (e.g., 384 and 864 wells) are also available.

An important microplate application exists in high-throughput organic synthesis (HTOS) systems. HTOS has been rapidly gaining importance as a tool for the accelerated synthesis of small organic molecules. HTOS systems employ a variety of automation techniques, which significantly reduce the time required for the development of commercially acceptable compounds in the pharmaceutical, agrochemical and other specialty chemical industries. Most conventional HTOS systems simultaneously synthesize large groups of compounds while using standard microplate assemblies for the reaction, purification and shipment of such compounds. Another important microplate application exists in high-throughput screening (HTS) systems, which examine samples of pre-dissolved compounds for desired properties. HTS systems usually examine the samples while they are contained in the wells of conventional microplates. As such, automatic apparatus must manipulate conventional microplates and their contents during a typical HTS process. Consequently, a primarily requirement of a microplate assembly for use in HTOS and HTS systems is an ability to securely maintain a controlled environment for a liquid sample while the assembly is being manipulated in an automation process. In addition, a microplate assembly must provide means for adding reagents or other materials to an individual well or to multiple wells simultaneously. Further, a microplate assembly must allow for the mechanical mixing of well contents without risking spills, leaks or cross contamination.

Many HTOS systems deliver multiple samples as solutions of pre-dissolved compounds in microplate assemblies to various locations throughout the world. To prevent a loss of these solutions of pre-dissolved compounds from occurring during delivery, suppliers often convert the solutions into solids prior to shipment by freezing or other methods. Shipping compounds as solids rather than liquids, however, creates problems in dissolution that can complicate and inhibit subsequent sample evaluation procedures. Further, an unstable solid material may disperse on opening of a closed well prior to re-dissolution. Consequently, those skilled in the art have recognized that HTOS systems should preferably deliver solutions of compounds in their stable liquid form.

A need to deliver compounds as stable liquids creates handling and storage requirements that standard microplate apparatus cannot fully provide. As mentioned above, spills, leaks, sample evaporations and well contamination often limit the application of most standard microplate assemblies in high-throughput systems. A singular example involves the shipping of microplate assemblies in aircraft cargo hulls. At flying altitudes, a low ambient air pressure in an aircraft cargo hull may create a relatively large pressure difference across a well closure. Such pressure differences often cause press-fit closures to distort or even pop open, thereby permitting a resident liquid sample to spill, leak, evaporate, and/or cross contaminate other open wells. Similar problems also occur in conventional surface shipping because of mechanical shocks, vibrations and the like. Likewise, some chemical reactions create heat and pressure of sufficient magnitude in the confines of a sealed well such that the well closure will inadvertently open, thereby causing a resident sample to leak.

One attempt to resolve the shipping problems described above involves the use of a solution of a compound in an assay-compatible solvent that can be frozen, such as dimethyl sulfoxide. If the solution remains frozen, delivery may be achieved without spillage. This, unfortunately, is not always the case, since the useful life of cooling agents available for use in shipping environments rarely exceeds a few days. In addition, certain compounds will come out of solution on freezing and remain out on thawing, further complicating the use of cooling agents. Therefore, shipping techniques that involve cooling agents often create multiple sample-handling problems and require an inspection step prior to assay. Other attempts at solving these and similar problems have usually resulted in unduly complicating the structure of a microplate assembly while imposing elaborate and unacceptable requirements on automated processing systems.

SUMMARY OF THE INVENTION

The present invention solves these problems in the art by providing a technique for preventing the loss and contamination of the contents of microplate assemblies. In general, the present invention includes a method of sealing and venting a vessel having an opening and an interior volume containing a liquid sample. The method comprises the steps of inserting a plug in the opening, forming a vent in the interior of the vessel, and extending a tubular passage from the vent to the exterior of the vessel. The vent communicates with the interior volume and the exterior of the vessel. The method further includes extending the tubular passage through the plug. In addition, the liquid sample is deposited in a liquid-holding space in the interior volume. The liquid sample remains confined to the liquid-holding space for all orientations of the vessel. The vent communicates with the interior volume outside the liquid-holding space.

According to another aspect of the invention, a microplate assembly comprises a microplate having a plurality of open wells. Each of the wells comprises a vessel with an interior volume. A seal is coupled to the wells for sealing the wells so that liquid in the interior volume is prevented from exiting the wells. A vent equalizes the pressure of the wells with the ambient pressure.

Still, another aspect of the invention includes a microplate assembly comprising a multi-well microplate, a plurality of vent caps and a porous vent film. The microplate houses a plurality of open wells in a rectangular array. Vent caps seal and vent the wells. When the vent caps are coupled to the wells, an interior volume is formed in each well. The wells hold liquid samples that occupy predetermined spaces within the interior volumes. The liquid samples remain within a predetermined space for all orientations of the microplate assembly. The vent caps comprise sealing plugs and vent tubes, which are interconnected by a perforated web. The sealing plugs form a seal at the mouth of the open wells. The vent tubes attach to the sealing plugs and terminate in vents. The vents communicate with the interior volumes outside the predetermined spaces occupied by the liquid samples. The vents permit the pressure within the interior volume to be equalized with the ambient pressure via a passage that runs through the vent tube and the sealing plugs. Material may be added to or removed from the wells via the passages. The porous vent film, which has an adhesive coating, adheres to the vent caps while covering the passages, thereby inhibiting evaporation of the liquid samples.

BRIEF DESCRIPTION OF THE DRAWINGS

The teachings of the present invention can be readily understood by considering the following detailed description in conjunction with the accompanying drawings, in which.

DETAILED DESCRIPTION OF THE PREFERRED EMBODIMENT

Referring now to the drawings, microplate assembly 10 comprises microplate 11, four vent caps 12 and vent film 13. Microplate 11 includes a box-like frame having side walls 15 and rectangular top wall 16, which house an array of ninety-six wells 17 arranged in twelve rows and eight columns. Each vent cap 12 comprises a rectangular array of twenty-four well inserts 20 arranged in three rows and eight columns. Four sets of well inserts 20 mate with corresponding wells 17 in the manner illustrated in FIG. 2, such that each of the ninety-six wells 17 contains a corresponding well insert 20. Vent film 13 comprises an adhesive-backed, porous film that adheres to the upper surface of vent caps 12 in the manner depicted in FIG. 1.

Wells 17, which function as receptacles for liquid samples 19 (see FIGS. 8A–8C), are shaped like a conventional test tube, i.e., as a hollow, circular cylinder with open mouth 25. Mouths 25 lie in the plane of top wall 16 while the cylindrical axes of wells 17 extend parallel to each other and perpendicular to the plane of top wall 16. Microplate 11 illustrates a popular microplate configuration. However, as will become apparent from the following description, the present invention is applicable to a variety of conventional microplate configurations.

Figure 8A:
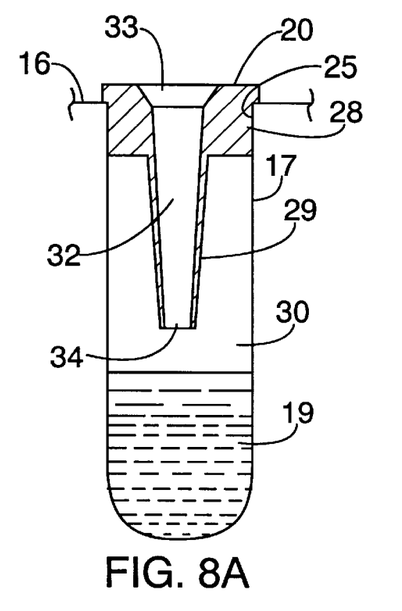
FIG. 8A depicts a diagrammatic cross-section of a well, illustrating the position of a liquid sample when the well assumes an upright position.
Figure 8B:
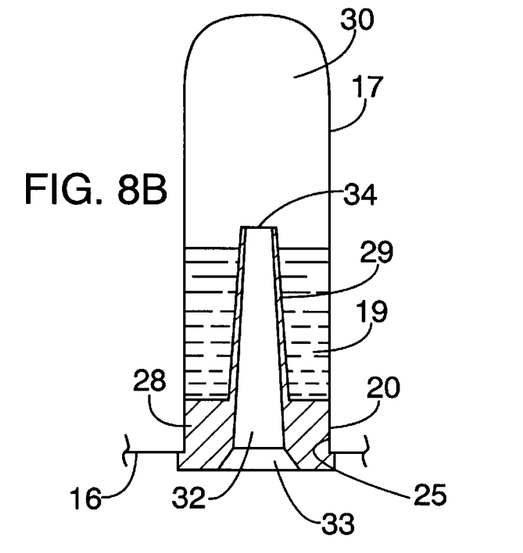
FIG. 8B depicts a diagrammatic cross-section of a well, illustrating the position of a liquid sample when the well assumes an inverted position.
Figure 8C:
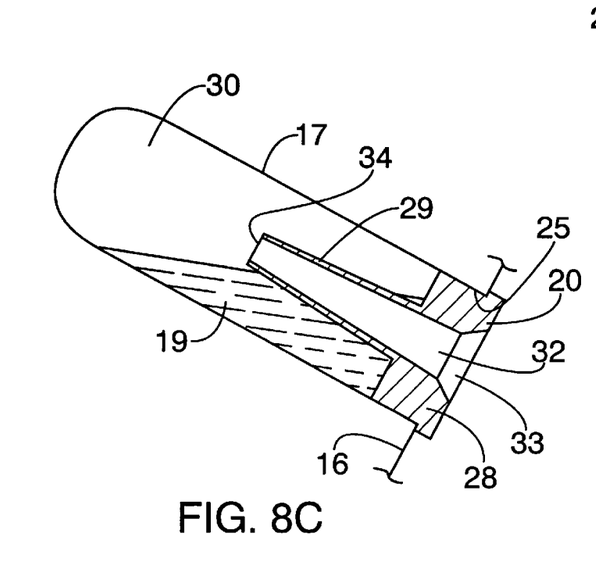
FIG. 8C depicts a diagrammatic cross-section of the well in FIGS. 8A and 8B, illustrating the position of a liquid sample when the well assumes an inclined position.

Vent caps 12 each comprise a plurality of well inserts 20 interconnected by perforated web 21. Each well insert 20 includes sealing plug 28 with attached vent tube 29. Passage 32 extends through vent tube 29 and sealing plug 28. Passage 32 terminates in vent 34 at its lower end. Vent tube 29, sealing plug 28 and the interior walls of well 17 form interior volume 30 in which liquid sample 19 is deposited. Liquid sample 19 will occupy and remain confined to a liquid-holding space within volume 30 for all orientations of well 17. Vent 34 communicates with interior volume 30 at a point outside of the liquid-holding space. FIGS. 8A–8C diagrammatically illustrate this feature. In FIG. 8A, which shows well 17 in an upright position, liquid sample 19 occupies a region of interior volume 30 that is spaced below vent 34. In FIG. 8B, which shows well 17 in an inverted position, liquid sample 19 occupies a region of interior volume 30 that is again spaced below vent 34. In FIG. 8C, which shows well 17 in an inclined position, liquid sample 19 continues to occupy a region of interior volume 30 that is again spaced below vent 34.

Figure 3:
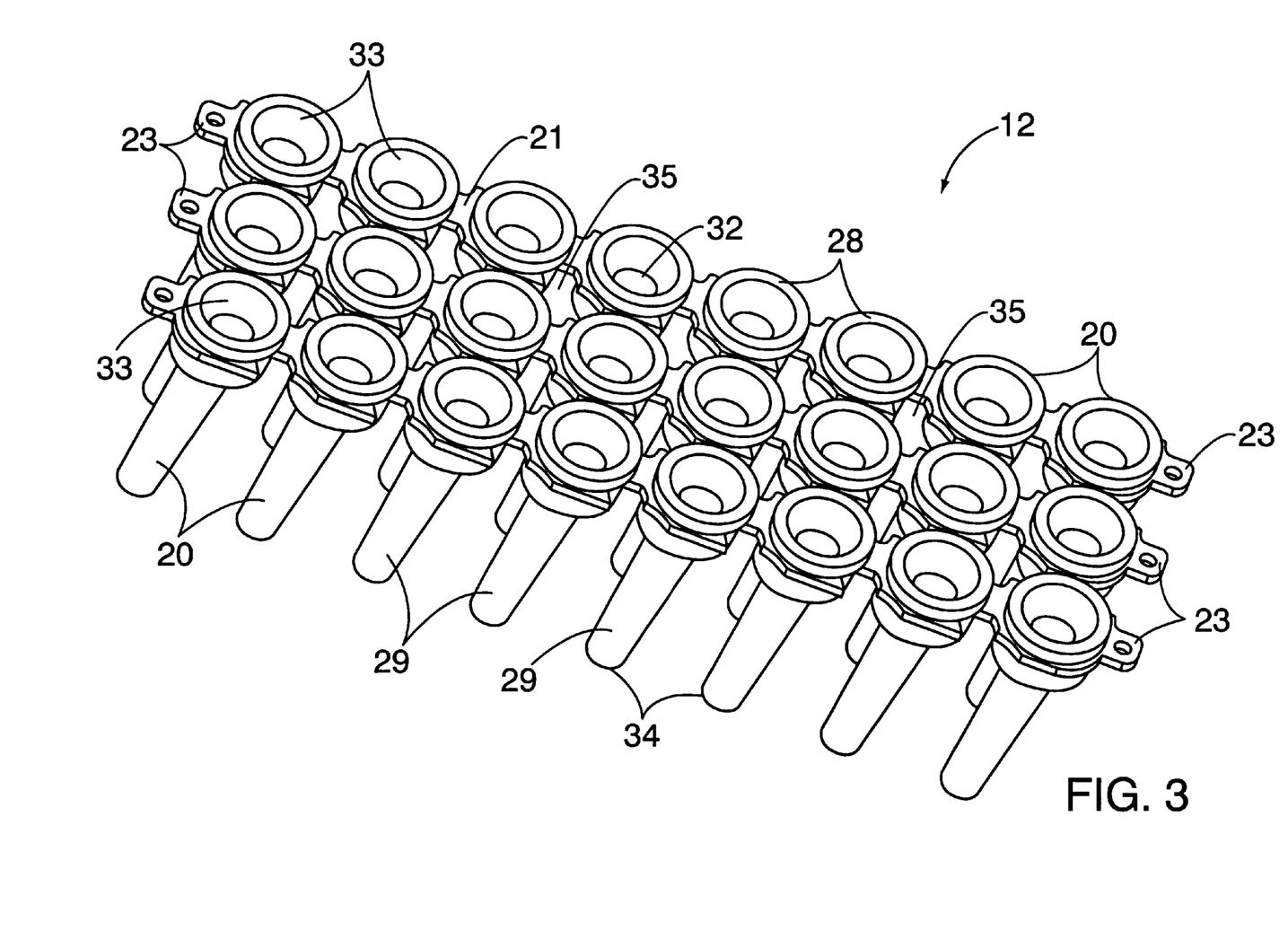
FIG. 3 is a pictorial view of a vent cap viewed from above, which forms a part of the microplate assembly illustrated in FIGS. 1 and 2.
Figure 4:
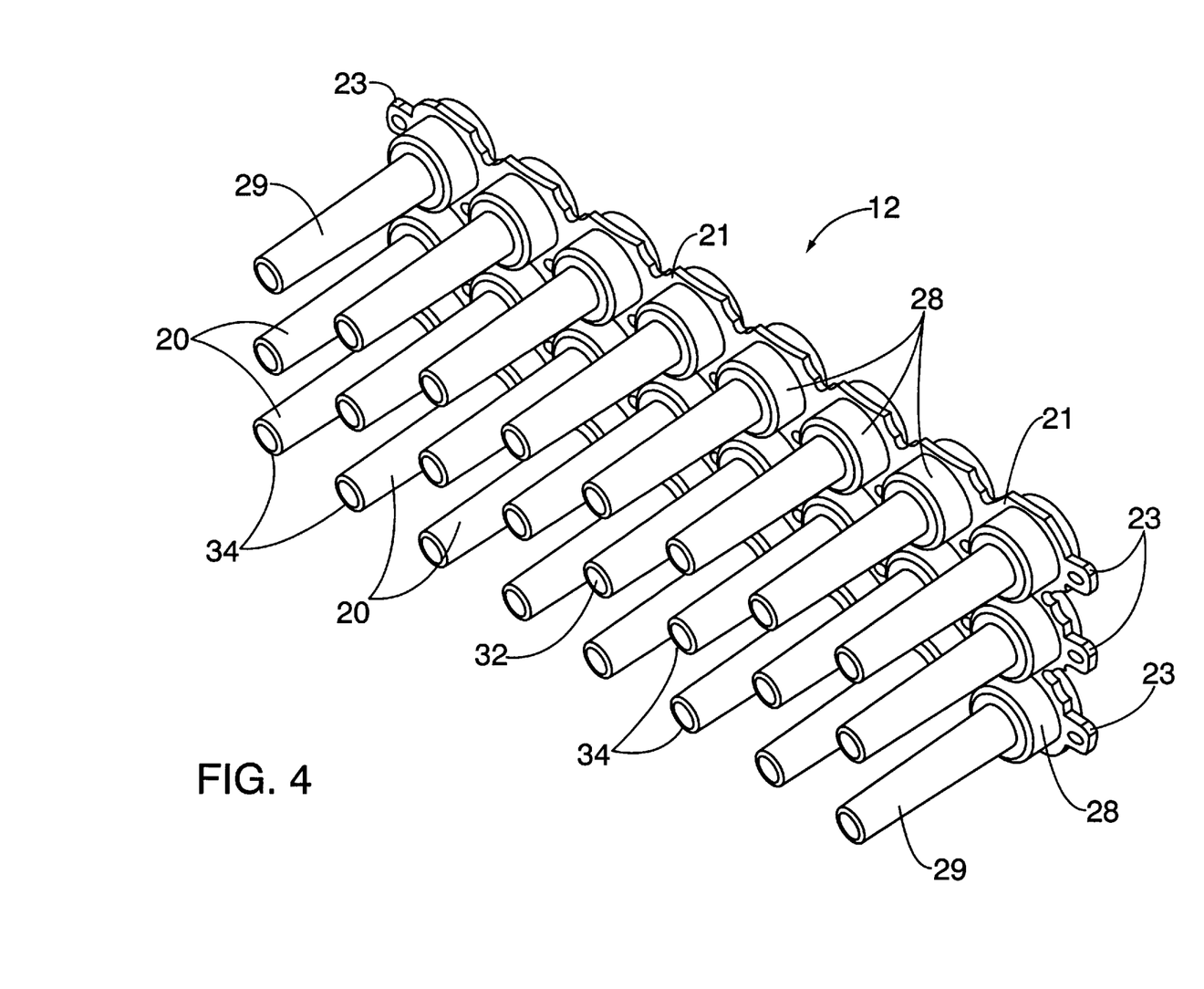
FIG. 4 illustrates the vent cap of FIG. 3 in a pictorial view as seen from below.
Figure 5:
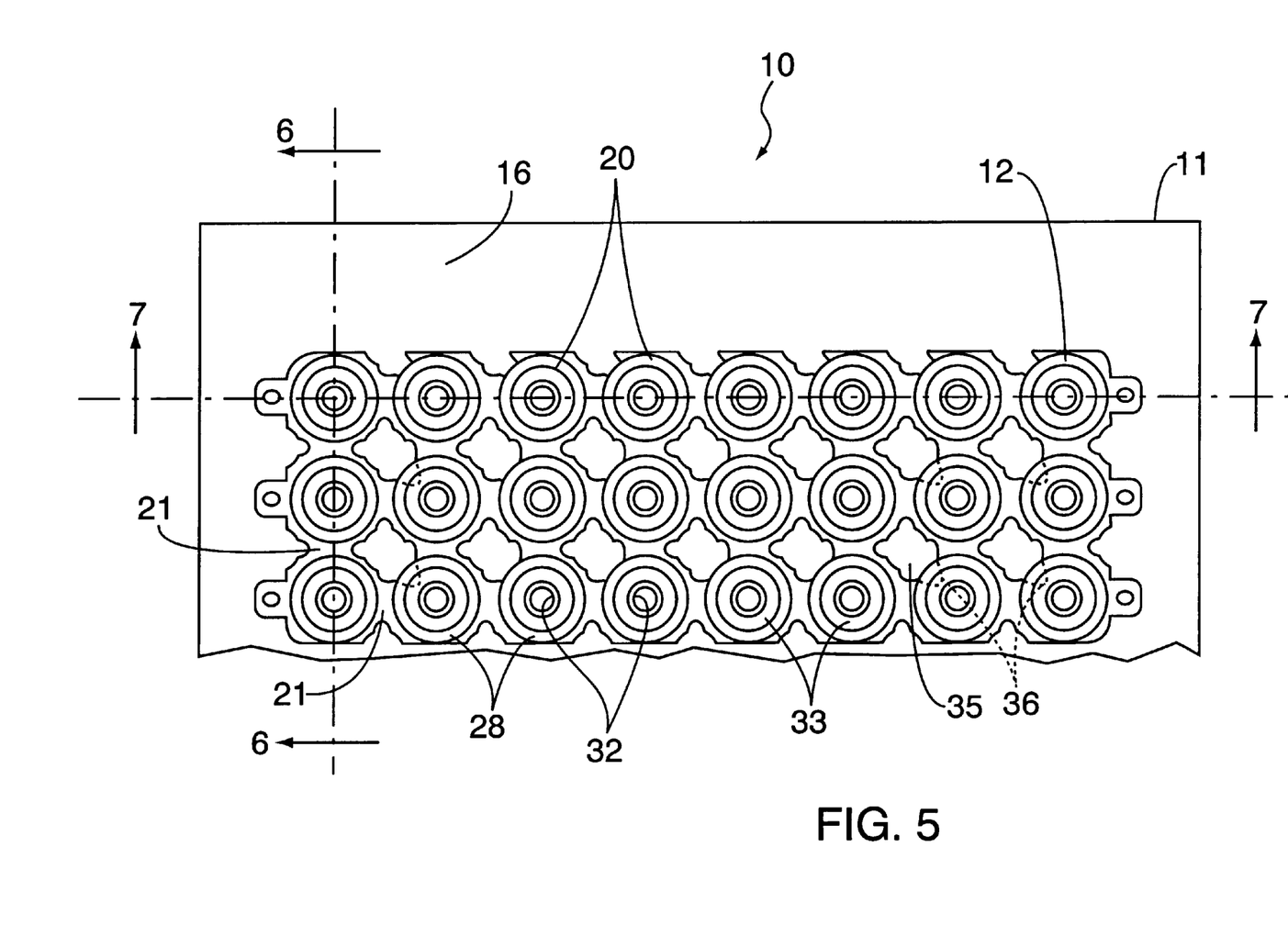
FIG. 5 depicts a break-away, top plan view of a portion of the microplate assembly of FIGS. 1 and 2.
Figure 6:
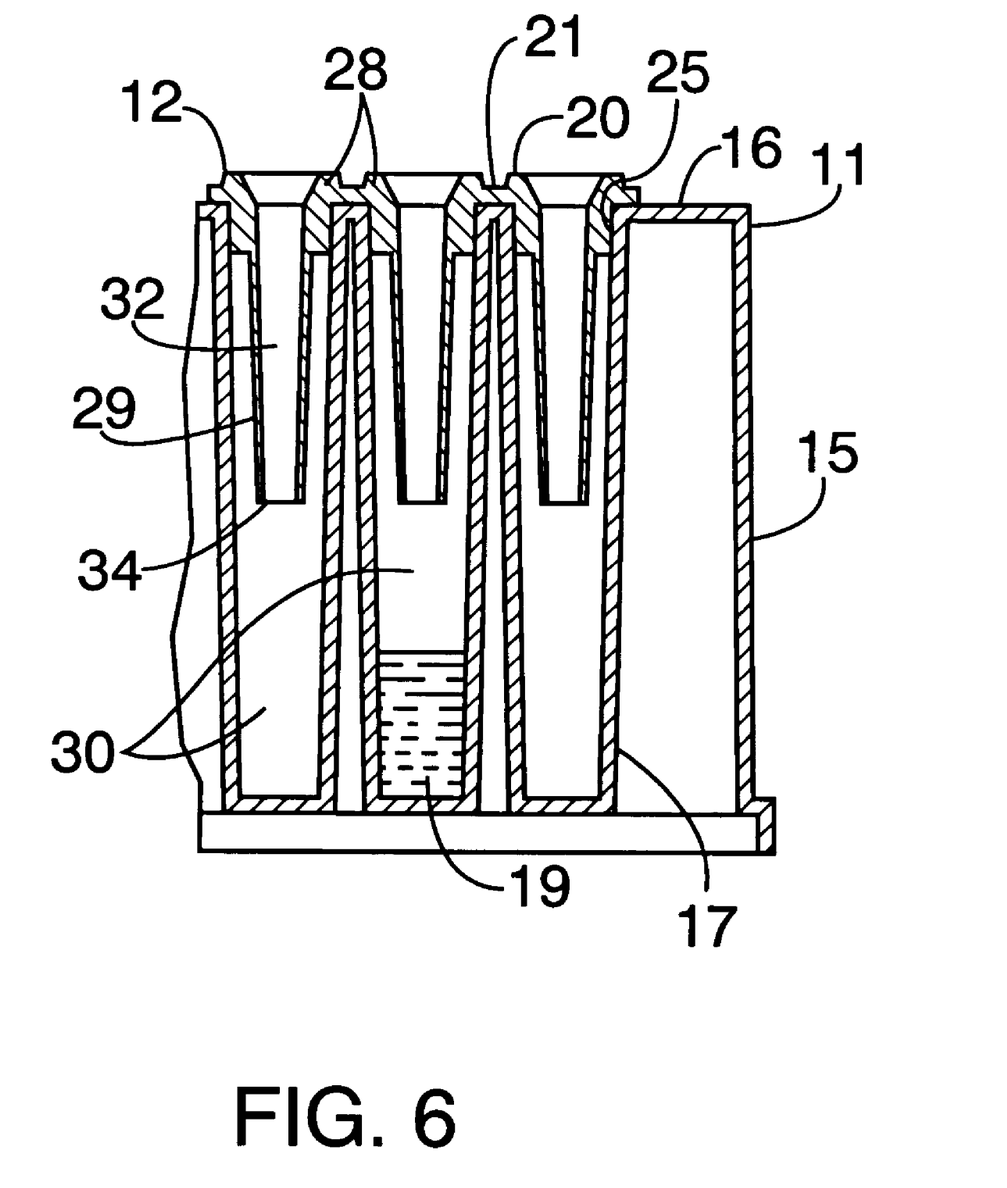
FIG. 6 is an elevation in cross section taken on the line 6—6 of FIG. 5 and looking in the direction of the arrows.
Figure 7:
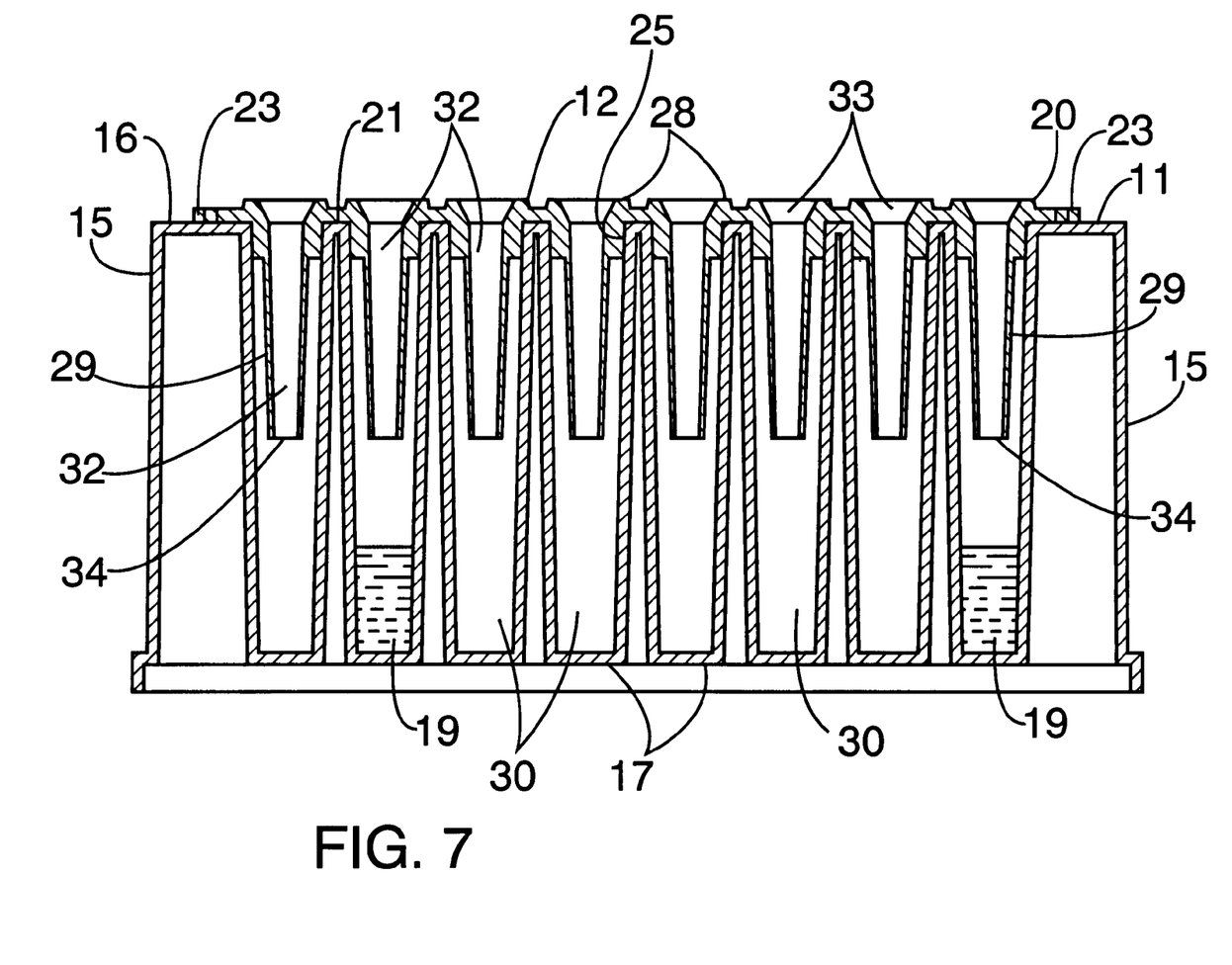
FIG. 7 is an elevation in cross section taken on the line 7—7 of FIG. 5 and looking in the direction of the arrows.

Passages 32, which pass through well inserts 20, include fluted aperture 33 at its upper end. Plug 28, vent tube 29 and passage 32 generally have circular cross-sections with a radial taper. Perforated web 21 attaches to plugs 28 to hold well inserts 20 in a rectangular array. A similar array of perforations 35 in web 21 appear amid well inserts 20. The underside of most plugs 28 includes notches 36, which provide sites where a rigid rod (not shown) may be inserted to help pry plugs 28 from their corresponding wells 17 when removing vent cap 12 from microplate 11.

Consequently, vent caps 12 function as multiple vented seals for interior volumes 30 of wells 17. Each well insert 20 couples with a different well 17 such that plug 28 forms a tight press-fit seal with the edge of mouth 25. With vent cap 12 properly coupled to wells 17, each plug 28 prevents liquid sample 19 from exiting the interior volume 30 via the seam at the interface between plug 28 and mouth 25. In addition, each vent 34 will permit the pressure within interior volume 30 to be equalized with the ambient pressure via passage 32, thereby avoiding forces that may dislodge plug 28.

Manufacturers may readily choose appropriate dimensions for vent caps 12 so that the location of liquid sample 19 will always be spaced from vent 34. Specifically, liquid sample 19 will remain in a liquid-holding space in interior volume 30 that will remain below vent 34 for all possible positions of microplate assembly 10. Consequently, sealing plug 28 and its associated vent tube 29 will function to prevent loss of liquid sample 19. Further, the shape and size of vent 34 and passage 32 make it difficult for liquid to exit passage 32 due to fluid surface tension. Therefore, during all but the most violent movements of microplate assembly 10, liquid sample 19 will remain in its liquid-holding space far removed from vent 34.

The effective volume of well 17 essentially equals the maximum volume that liquid sample 19 may occupy without engaging vent 34 for all possible orientations of microplate assembly 10. The effective volume may be maximized for a given well 17 by placing vent 34 at the centroid of interior volume 30. When vent 34 is placed at the centroid of interior volume 30, the maximum effective volume substantially equals one-half the interior volume 30.

Figure 1:
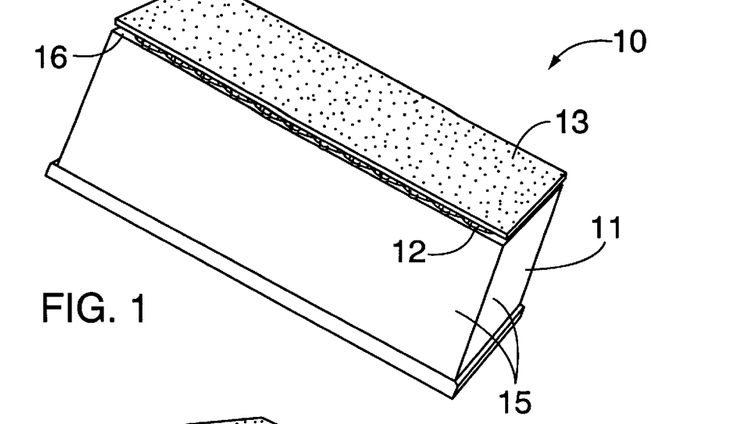
FIG. 1 is a pictorial view of a microplate assembly in accordance with the present invention.
Figure 2:
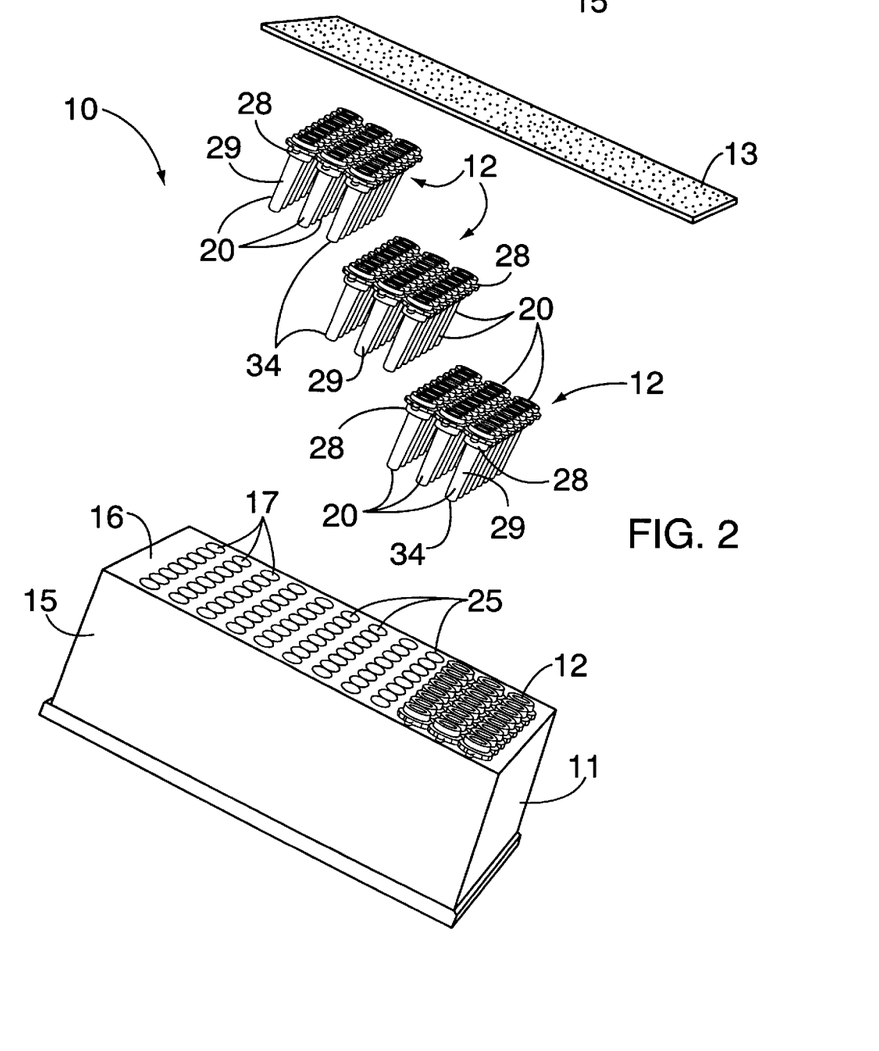
FIG. 2 is an exploded pictorial view of the microplate assembly of FIG. 1, showing a vent film, four vent caps and a microplate in accordance with the present invention.

As mentioned above, it is desirable that microplate assemblies 10 provide means for inhibiting evaporation of liquid samples 19. To this end, microplate assemblies 10 include adhesive vent films 13, which adhere to the upper surfaces of vent caps 12, as illustrated in FIG. 1. By blocking passage 32, vent films 13 inhibit evaporation by reducing air circulation within passages 32 and the interior volumes 30. Also, vent film 13, can block the entrance of contaminants into wells 17. Vent films 13 may be formed by coating a thin sheet of polyethylene with an appropriate adhesive. Vent films 13 may be rendered porous by punching relatively small holes in the adhesive sheets. The number of holes and their placement may be chosen so that each passage 32 will communicate with at least one hole. In addition, minimum sized vents 34 can also significantly inhibit evaporation.

Figure 9:
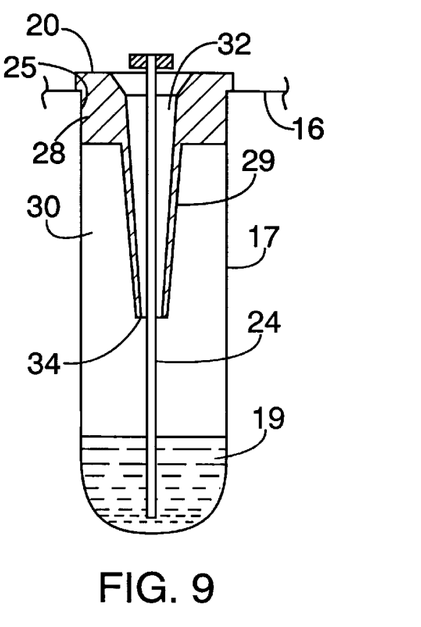
FIG. 9 depicts a diagrammatic cross-section of a probe inserted in a well.

Microplate assembly 10 includes features that make it suitable for use in a variety of processes. Passages 32 permit the addition of material to interior volume 30 without requiring that vent caps 12 be removed, altered or otherwise manipulated. Such materials may be added to wells 17 as a liquid, a gas or a solid. In the later case, of course, the solid must be dimensioned to permit movement through passage 32. As illustrated in FIG. 9, liquids may be injected into wells 17 with the aid of injection probe 24. Solids, e.g., pellets or powders, may also be deposited via passages 32. Gases may also be directed into wells 17 via passages 32 using probes or other gas injection apparatus to provide, for example, a special environment in volume 30.

Microplate assembly 10 is useful in either manual or automatic processes. For instance, passages 32 provide a convenient avenue through which material may be inserted manually into wells 17, with or without the use of probe 24 or other apparatus. In this regard, passages 32 may act as funnels to help lead the material into interior volume 30. On the other hand, most automation processes use one or more probes 24 to add material or remove material via suction. In this instance, fluted apertures 33 will aid the automation process by acting as self-centering guides that can easily direct probe 24 into passages 32. A splined probe or one that is narrower than vent 34 will allow venting to occur during liquid injection or aspiration. Alternatively, vents 34 may be fabricated with polygonal cross-sections to prevent round probes from inhibiting venting of interior volume 30.

As mentioned above, manufactures typically fabricate microplates from polystyrene, polycarbonate, polypropylene, Teflon, glass, ceramics or quartz. As such, vent caps 12 may be readily molded from a variety of compatible materials. In this regard, the materials of vent cap 12 must be such that plugs 28 will have sufficient resiliency to form a good press-fit seal with mouth 25. In addition, web 21 preferably flex to allow for easy positioning and removal of vent cap 12. Web 21 comprises end tabs 23, which may be gripped manually or mechanically when manipulating vent cap 12. As mentioned above, notches 36 provide additional assistance when removing vent cap 12 from wells 17.

While standard microplates come in a variety of sizes, most conventional microplates contain wells arranged in units of twenty-four, with each unit having a 3×8 well geometry. To render vent caps 12 useful with most conventional microplates, vent caps 12 preferably contain twenty-four well inserts 20 arranged in 3×8 geometry. As such, a user may apply one or more vent caps 12 to cover the wells in most conventional microplates. Moreover, a user may cut web 21 with an ordinary scissors to produce a well cap of a different shape and/or size. Likewise, a user may remove a single well insert 20 from vent cap 12 for use with an individual well 17.

Microplate assembly 10 will function suitably with most conventional mixing equipment. In many conventional processes, the well contents must be mixed. In most processes, the product is added first, the well is then sealed and, finally, the well contents are mixed. Some processes perform mixing with shakers that vibrate the microplate in a horizontal plane. Others turn or roll the microplate about a horizontal or inclined axis to effect mixing. In either case, when capping wells 17 with vent caps 12, a process can perform a mixing step immediately after adding a product without fear of loosing the product during mixing.

Consequently, a user can ship, synthesize, heat, shake and roll liquid samples 19 and not worry about loosing valuable product. Suppliers can feel comfortable about shipping their compounds in ready-to-use microplates. Freezing samples and dry shipping are avoided. Robotic equipment, for example, can manipulate microplate assemblies 10 into any desired position without spillage, thereby permitting a more efficient use of such equipment.

Of course, various other modifications and variations are contemplated and may obviously be resorted to in light of the present disclosure. It is to be understood, therefore, that within the scope of the appended claims, the invention may be practiced otherwise than as specifically described.

What is claimed is:

1. A liquid holding apparatus comprising:
   a fluid vessel having an opening and an interior volume with a liquid-holding space located therein; and
   a vent cap having means for equalizing gas pressure between said interior volume and the exterior of said fluid vessel and for sealing said opening against the independent passage of liquid from said interior volume to said exterior of said vessel for all possible positions of said vessel, said vent cap including:
   a press-fit plug mounted in said opening and having a flexible body with a resilient outer surface forming a friction-tight impermeable seal with an inside surface of said opening,
   a vent tube having first and second ends, said first end of said vent tube fixed to said press-fit plug and communicating with the exterior of said vessel, said second end of said vent tube extending into said interior volume and comprising a vent hole communicating with said interior volume outside said liquid-holding space for all said possible positions of said vessel, and
   a passage running from said vent hole through said vent tube and said body of said press-fit plug.

2. The apparatus of claim 1 wherein said vent hole is substantially located at the centroid of said interior volume.

3. The apparatus of claim 2 further including a porous vent film mounted on said press-fit plug and covering said passage, and wherein said press-fit plug and said vent tube are molded as a unitary structure.

4. A microplate assembly comprising:
   a microplate having a rigid body with a plurality of open wells mounted therein, each of said open wells comprising a fluid vessel with an opening and an interior volume with a liquid-holding space located therein; and
   a vent cap having means for equalizing gas pressure between said interior volume and the exterior of said vessel and for sealing the plurality of open wells simultaneously to prevent the independent passage of liquid from said interior volume to said exterior of said vessel for all possible orientations of said vessel, the vent cap including:
   a plurality of press-fit plugs each having a flexible body with a resilient outer surface mounted in a different one of said openings, and each said resilient outer surface forming a friction-tight impermeable seal with an inside surface of a corresponding one of said openings,
   vent tubes each having first and second ends, said first end of each said vent tube fixed to a different one of said press-fit plugs and communicating with the exterior of said vessel, said second end of each said vent tube comprising a vent hole communicating with the interior volume outside said liquid-holding space for all possible orientations of said assembly,
   a passage running from said vent hole through said vent tube and said body of each said press-fit plug, and
   a flexible sheet connected to said plurality of press-fit plugs.

5. The microplate assembly of claim 4 wherein said vent hole is substantially located at the centroid of said interior volume.

6. The microplate assembly of claim 5 wherein said openings define a first plane and said flexible sheet defines a second plane parallel to and superimposed on said first plane, and further including perforations located in said flexible sheet to form a planar web connected to said resilient outer surface of each said press-fit plug such that said passages are substantially parallel to each other and perpendicular to said first plane.

7. The microplate assembly of claim 6 further including a porous vent film mounted on said press-fit plugs and covering said passages, and wherein said vent cap is molded as a unitary structure.

8. A vent cap for sealing an opening in a fluid vessel having an interior volume with a liquid-holding space located therein, said vent cap equalizing gas pressure between said interior volume and the exterior of said vessel and preventing the independent passage of liquid from said interior volume to said exterior of said vessel for all possible positions of said vessel, said vent cap comprising:
   a press-fit plug having a flexible body with a resilient outer surface capable of forming a friction-tight impermeable seal with an inside surface of said opening;
   a vent tube having first and second ends, said first end of said vent tube fixed to said press-fit plug to communicate with said exterior of said vessel, said second end of said vent tube comprising a vent hole to communicate with said interior volume outside said liquid-holding space for said all possible positions of said vessel; and
   a passage running from said vent hole through said vent tube and said body of said press-fit plug.

9. The vent cap of claim 8 further including a porous vent film mounted on said press-fit plug and covering said passage.

10. The vent cap of claim 9 wherein said press-fit plug and said vent tube are molded as a unitary structure.

11. A vent cap for sealing openings in multiple open fluid vessels arranged in a predetermined pattern, each said fluid vessel having an interior volume with a liquid-holding space located therein, said vent cap equalizing gas pressure between said interior volumes and the exterior of said vessels and preventing the independent passage of liquid from said interior volumes to said exterior of said vessels for all possible positions of said vessels, said vent cap comprising:
   a plurality of press-fit plugs each having a flexible body with a resilient outer surface capable of forming a friction-tight impermeable seal with an inside surface of said opening;
   a plurality of vent tubes each having first and second ends, said first end of each said vent tube fixed to a different one of said press-fit plugs for communicating with said exterior of said vessels, said second end of each said vent tub comprising a vent hole communicating with said interior volume outside said liquid-holding space for said all possible positions of said vessels;
   a passage running from each said vent hole through each said vent tube and each said press-fit plug; and
   a flexible sheet connected to said plurality of press-fit plugs and holding said press-fit plugs in a pattern corresponding to said predetermined pattern.

12. The vent cap of claim 11 further including at least one pull tab mounted on the periphery of said flexible sheet, and wherein said flexible sheet includes perforations to form a planar web connected to said press-fit plugs, said web mounting said press-fit plugs in a common plane such that the longitudinal axes of said vent tubes are parallel to each other and perpendicular to said common plane.

13. The vent cap of claim 12 wherein said web, said press-fit plugs and said vent tubes are molded into a unitary structure.

14. A method of sealing a vessel, to prevent the independent passage of liquid from said vessel for all possible positions of said vessel, and venting said vessel, to equalize the gas pressure between the interior and exterior of said vessel, and wherein said vessel has an opening and an interior volume with a liquid-holding space located therein, said method comprising:

inserting a press-fit plug having a flexible body with a resilient outer surface in said opening to form a friction-tight impermeable seal between said outer surface and an inside surface of said opening;

forming a vent hole in said interior of said vessel outside said liquid holding space for all possible positions of said vessel; and extending a tubular passage from said vent hole through said flexible body of said press-fit plug to the exterior of said vessel such that said vent hole communicates with said interior volume outside said liquid-holding space and said exterior of said vessel.

15. The method of claim 14 further including placing a liquid sample in said liquid-holding space in said interior volume such that said liquid sample occupies said liquid-holding space for all orientations of said vessel, and wherein said forming step includes placing said vent hole in communication with said interior volume outside said liquid-holding space.

16. The method of claim 15 wherein said forming step includes placing said vent hole at substantially the centroid of said interior volume.

17. A method of sealing and venting multiple open wells contained in a multi-well microplate, each said well comprising a fluid vessel with an opening, an interior volume and a liquid-holding space located in said interior volume, said wells being sealed to prevent the independent passage of liquid from said liquid-holding space to the exterior of said vessel, said method comprising the steps of:

inserting a press-fit plug having a flexible body with a resilient outer surface in each of said openings to form a friction-tight impermeable seal between said outer surface and an inside surface of said opening;

forming a vent hole in the interior volume of each of said wells outside said liquid-holding spaces for all possible positions of said wells;

extending a passage from each said vent hole through the flexible body of each said press-fit plug to the exterior of said wells; and joining said press-fit plugs to each other with a flexible sheet in a planar array to match a pattern of said open wells.

18. The method of claim 17 further including placing a liquid sample in each said liquid-holding space for all orientations of said microplate, and wherein said forming step includes placing each said vent hole in communication with said interior volume outside said liquid-holding space.

19. The method of claim 18 wherein said forming step includes placing each said vent hole at substantially the centroid of said interior volume.

* * * * *